United States Patent
Boneau

(12) 
(10) Patent No.: US 6,344,053 B1
(45) Date of Patent: Feb. 5, 2002

(54) ENDOVASCULAR SUPPORT DEVICE AND METHOD

(75) Inventor: Michael D. Boneau, Campbell, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 45 days.

(21) Appl. No.: 09/287,216

(22) Filed: Apr. 5, 1999

Related U.S. Application Data

(60) Continuation of application No. 08/471,738, filed on Jun. 6, 1995, now Pat. No. 5,891,190, which is a division of application No. 08/172,420, filed on Dec. 22, 1993, now abandoned, which is a division of application No. 07/398,180, filed on Aug. 24, 1999, now Pat. No. 5,292,331.

(51) Int. Cl.$^7$ .................................................. A61F 2/04
(52) U.S. Cl. ...................................... 623/1.11; 606/198
(58) Field of Search ............................... 623/1.11, 1.15; 606/198

(56) References Cited

U.S. PATENT DOCUMENTS

| | | | |
|---|---|---|---|
| 2,070,073 A | 2/1937 | Walton | |
| 2,701,559 A | 2/1955 | Cooper | |
| 2,854,982 A | 10/1958 | Pagano | |

(List continued on next page.)

FOREIGN PATENT DOCUMENTS

| | | |
|---|---|---|
| AU | A-23784/88 | 4/1989 |
| AU | B-53198/94 | 8/1989 |
| AU | B-61333/90 | 8/1989 |
| DE | 2410933 | 9/1974 |

(List continued on next page.)

OTHER PUBLICATIONS

Charnsangavej C., M.D., et al., "A New Expandable Metallic Stent for Dilation of Stenotic Tubular Structures: Experimental and Clinical Evaluation," *Houston Medical Journal* 1987; 3: 41–52.

Culverwell M., "Angioplasty Stents May Prevent Restenosis," *Carcio* 1987; Jan.; 11–13.

Palmaz J.C., M.D., et al., "Atherosclerotic Rabbit Aortas: Expandable Intraluminal Grafting," *Radiology* 1986; 3: 723–726.

Schatz R., M.D., et al., "Balloon–expandable intracoronary stents in the adult dog," *Circulation* 1987; 76: 450–457.

Palmaz J.C., "Die intraluminale Sten–Implantation nach Palmaz," *Radiologe* 1987; 11: 560–563.

Roubin G., et al., "Early and late results of intracoronary arterial stenting after coronary angioplasty in dogs," *Circulation* 1987; 4: 891–897.

Fallone B.G., PhD., "Elastic Characteristics of the Self–expanding Metallic Stents," *Investigative Radiology* 1988; 23: 370–376.

(List continued on next page.)

*Primary Examiner*—David H. Willse
*Assistant Examiner*—Suzette J. Jackson
(74) *Attorney, Agent, or Firm*—Sterne, Kessler, Goldstein & Fox, P.L.L.C.

(57) ABSTRACT

An endovascular support device for treatment of chronic restenosis or other vascular narrowing is disclosed together with a method of manufacture and a method for delivering a plurality of such devices to an affected area of a vessel. In a preferred embodiment, the endovascular support device comprises a unitary wire-like structure configured to form a plurality of upper and lower peaks which may be compressed for delivery to an affected area of a coronary or peripheral vessel in a human, and then expanded to maintain a passageway through the vessel.

30 Claims, 4 Drawing Sheets

U.S. PATENT DOCUMENTS

| | | |
|---|---|---|
| 2,854,983 A | 10/1958 | Baskin |
| 3,105,492 A | 10/1963 | Jeckel |
| 3,155,095 A | 11/1964 | Brown |
| 3,284,762 A | 11/1966 | Kompanek |
| 3,334,629 A | 8/1967 | Cohn |
| 3,526,005 A | 9/1970 | Bokros et al. |
| 3,540,431 A | 11/1970 | Mobin-Uddin |
| 3,562,820 A | 2/1971 | Braun |
| 3,599,641 A | 8/1971 | Sheridan |
| 3,657,744 A | 4/1972 | Ersek |
| 3,713,175 A | 1/1973 | Weisman |
| 3,714,671 A | 2/1973 | Edwards et al. |
| 3,774,596 A | 11/1973 | Cook |
| 3,834,394 A | 9/1974 | Hunter et al. |
| 3,858,441 A | 1/1975 | Comeau et al. |
| 3,868,956 A | 3/1975 | Alfidi et al. |
| 3,874,388 A | 4/1975 | King et al. |
| 3,882,845 A | 5/1975 | Bucalo |
| 3,889,685 A | 6/1975 | Miller, Jr. et al. |
| 3,893,344 A | 7/1975 | Dantlgraber et al. |
| 3,894,974 A | 7/1975 | Hunter et al. |
| 3,952,747 A | 4/1976 | Kimmell, Jr. |
| 3,968,800 A | 7/1976 | Vilasi |
| 4,038,702 A | 8/1977 | Sawyer |
| 4,047,252 A | 9/1977 | Liebig et al. |
| 4,056,854 A | 11/1977 | Boretos et al. |
| 4,061,134 A | 12/1977 | Samuels et al. |
| 4,065,816 A | 1/1978 | Sawyer |
| 4,076,285 A | 2/1978 | Martinez |
| 4,080,706 A | 3/1978 | Heilman et al. |
| 4,105,022 A | 8/1978 | Antoshkiw et al. |
| 4,106,129 A | 8/1978 | Carpentier et al. |
| 4,140,126 A | 2/1979 | Choudhury |
| 4,159,719 A | 7/1979 | Haerr |
| 4,183,102 A | 1/1980 | Guiset |
| 4,190,909 A | 3/1980 | Ablaza |
| 4,195,637 A | 4/1980 | Gruntzig et al. |
| 4,198,982 A | 4/1980 | Fortner et al. |
| 4,214,587 A | 7/1980 | Sakura |
| 4,276,132 A | 6/1981 | Fettel et al. |
| 4,295,464 A | 10/1981 | Shihata |
| 4,299,226 A | 11/1981 | Banka |
| 4,300,244 A | 11/1981 | Bokros |
| 4,313,231 A | 2/1982 | Koyamada |
| 4,319,363 A | 3/1982 | Ketharanathan |
| 4,323,994 A | 4/1982 | Coogler |
| 4,328,811 A | 5/1982 | Fogarty |
| 4,338,942 A | 7/1982 | Fogarty |
| 4,340,046 A | 7/1982 | Cox |
| 4,343,048 A | 8/1982 | Ross et al. |
| 4,343,049 A | 8/1982 | Fettel et al. |
| 4,390,599 A | 6/1983 | Broyles |
| 4,402,307 A | 9/1983 | Hanson et al. |
| 4,403,612 A | 9/1983 | Fogarty |
| 4,733,665 C1 | 1/1984 | Palmaz |
| 4,448,195 A | 5/1984 | LeVeen et al. |
| 4,479,497 A | 10/1984 | Fogarty et al. |
| 4,483,340 A | 11/1984 | Fogarty et al. |
| 4,493,711 A | 1/1985 | Chin et al. |
| 4,494,531 A | 1/1985 | Gianturco |
| 4,503,569 A | 3/1985 | Dotter |
| 4,512,338 A | 4/1985 | Balko et al. |
| 4,531,933 A | 7/1985 | Norton et al. |
| 4,550,447 A | 11/1985 | Seiler, Jr. et al. |
| 4,553,545 A | 11/1985 | Maass et al. |
| 4,560,374 A | 12/1985 | Hammerslag |
| 4,562,596 A | 1/1986 | Kornberg |
| 4,572,186 A | 2/1986 | Gould et al. |
| 4,577,631 A | 3/1986 | Kreamer |
| 4,580,568 A * | 4/1986 | Gianturco .................. 623/1.15 |
| 4,586,505 A | 5/1986 | Sisson et al. |
| 4,604,762 A | 8/1986 | Robinson |
| 4,617,932 A | 10/1986 | Kornberg |
| 4,619,246 A | 10/1986 | Molgaard-Nielsen et al. |
| 4,619,261 A | 10/1986 | Guerriero |
| 4,641,653 A | 2/1987 | Rockey |
| 4,643,184 A | 2/1987 | Mobin-Uddin |
| 4,647,416 A | 3/1987 | Seiler, Jr. et al. |
| 4,649,922 A | 3/1987 | Wiktor ...................... 128/344 |
| 4,649,922 C1 * | 3/1987 | Wiktor ...................... 128/344 |
| 4,650,466 A | 3/1987 | Luther |
| 4,655,771 A | 4/1987 | Wallsten |
| 4,660,559 A | 4/1987 | McGregor et al. |
| 4,660,560 A | 4/1987 | Klein |
| 4,665,918 A | 5/1987 | Garza et al. |
| 4,670,734 A | 6/1987 | Caddock |
| 4,673,409 A | 6/1987 | Van Kampen |
| 4,676,241 A | 6/1987 | Webb et al. |
| 4,680,031 A | 7/1987 | Alonso |
| 4,681,110 A | 7/1987 | Wiktor |
| 4,699,611 A | 10/1987 | Bowden |
| 4,704,126 A | 11/1987 | Baswell et al. |
| 4,705,517 A | 11/1987 | DiPisa, Jr. |
| 4,706,671 A | 11/1987 | Weinrib |
| 4,710,181 A | 12/1987 | Fuqua |
| 4,723,549 A | 2/1988 | Wholey et al. |
| 4,731,054 A | 3/1988 | Billeter et al. |
| 4,733,665 A | 3/1988 | Palmaz |
| 4,739,762 A * | 4/1988 | Palmaz ...................... 128/343 |
| 4,740,207 A | 4/1988 | Kreamer |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,771,773 A | 9/1988 | Kropf |
| 4,775,426 A | 10/1988 | Murley et al. |
| 4,776,337 A | 10/1988 | Palmaz |
| 4,787,899 A | 11/1988 | Lazarus |
| 4,793,348 A | 12/1988 | Palmaz |
| 4,794,928 A | 1/1989 | Kletschka |
| 4,795,458 A | 1/1989 | Regan |
| 4,800,882 A | 1/1989 | Gianturco |
| 4,813,925 A | 3/1989 | Anderson, Jr. et al. |
| 4,830,003 A | 5/1989 | Wolff et al. |
| 4,842,575 A | 6/1989 | Hoffman, Jr. et al. |
| 4,848,343 A | 7/1989 | Wallsten et al. |
| 4,856,516 A | 8/1989 | Hillstead |
| 4,869,714 A | 9/1989 | Deininger et al. |
| 4,870,966 A | 10/1989 | Dellon et al. |
| 4,875,480 A | 10/1989 | Imbert |
| 4,877,030 A | 10/1989 | Beck et al. |
| 4,878,906 A | 11/1989 | Lindemann et al. |
| 4,886,062 A | 12/1989 | Wiktor |
| 4,892,539 A | 1/1990 | Koch |
| 4,892,541 A | 1/1990 | Alonso |
| 4,893,623 A | 1/1990 | Rosenbluth |
| 4,902,289 A | 2/1990 | Yannas |
| 4,907,336 A | 3/1990 | Gianturco |
| 4,913,141 A | 4/1990 | Hillstead |
| 4,922,905 A | 5/1990 | Strecker |
| 4,923,464 A | 5/1990 | DiPisa, Jr. |
| 4,950,227 A | 8/1990 | Savin et al. |
| 4,954,126 A | 9/1990 | Wallsten |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,032 A | 2/1991 | Sugiyama et al. |
| 4,994,071 A | 2/1991 | MacGregor |
| 4,994,077 A | 2/1991 | Dobben |
| 4,998,539 A | 3/1991 | Delsanti |

| | | |
|---|---|---|
| 4,998,923 A | 3/1991 | Samson et al. |
| 5,002,560 A | 3/1991 | Machold et al. |
| 5,007,926 A | 4/1991 | Derbyshire |
| 5,015,253 A | 5/1991 | Macgregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A * | 7/1991 | Giantureo et al. ......... 623/1.15 |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,108,417 A | 4/1992 | Sawyer |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,163,958 A | 11/1992 | Pinchuk |
| 5,192,307 A | 3/1993 | Wall |
| 5,195,984 A | 3/1993 | Schatz |
| 5,201,901 A | 4/1993 | Harada |
| RE34,327 E | 7/1993 | Kreamer |
| 5,226,913 A | 7/1993 | Pinchuk |
| 5,236,447 A | 8/1993 | Kubo et al. |
| 5,266,073 A | 11/1993 | Wall |
| 5,275,622 A | 1/1994 | Lazarus |
| 5,282,824 A | 2/1994 | Gianturco |
| 5,282,848 A | 2/1994 | Schmitt |
| 5,292,331 A * | 3/1994 | Boneau ..................... 606/198 |
| 5,306,286 A | 4/1994 | Stack et al. |
| 5,314,444 A | 5/1994 | Gianturco |
| 5,342,348 A | 8/1994 | Kaplan |
| 5,382,261 A | 1/1995 | Palmaz |
| 5,383,892 A | 1/1995 | Cardon et al. |
| 5,397,345 A | 3/1995 | Lazarus |
| 5,421,955 C1 | 6/1995 | Lau et al. |
| 5,443,496 A | 8/1995 | Schwartz et al. |
| 5,507,767 A | 4/1996 | Maeda et al. |
| 5,507,768 A | 4/1996 | Lau et al. |
| 5,507,771 A | 4/1996 | Gianturco |
| 4,954,126 C1 | 5/1996 | Wallsten |
| 5,527,336 A | 6/1996 | Rosenbluth et al. |
| 5,549,635 A * | 8/1996 | Solar ......................... 623/1.11 |
| 4,655,771 C1 | 9/1996 | Wallsten |
| 5,556,413 A | 9/1996 | Lam |
| 5,562,728 A | 10/1996 | Lazarus |
| 5,569,295 A * | 10/1996 | Lam .......................... 623/1.11 |
| 5,591,197 A | 1/1997 | Orth et al. |
| 5,591,198 A * | 1/1997 | Boyle et al. ............... 623/1.11 |
| 5,618,299 A | 4/1997 | Khosravi et al. |
| 5,618,301 A | 4/1997 | Hauenstein |
| 5,653,727 A | 8/1997 | Wiktor |
| 5,662,700 A | 9/1997 | Lazarus |
| 5,669,936 A | 9/1997 | Lazarus |
| 5,674,278 A | 10/1997 | Boneau |
| 5,800,509 A | 9/1998 | Boneau |
| 4,739,762 C1 | 10/1998 | Palmaz ...................... 606/108 |
| 5,879,382 A | 3/1999 | Boneau |
| 5,891,190 A * | 4/1999 | Boneau ..................... 623/1.11 |
| 5,902,332 A | 5/1999 | Schatz |

FOREIGN PATENT DOCUMENTS

| | | |
|---|---|---|
| DE | 3205942 A1 | 9/1983 |
| DE | 3640745 A1 | 6/1987 |
| DE | 690 29 114 T 2 | 3/1997 |
| DK | EP 0417928 T3 | 12/1996 |
| EP | 0 183 372 | 6/1986 |
| EP | 0 177 330 | 9/1986 |
| EP | 0 274 846 A1 | 7/1988 |
| EP | 0 282 175 A1 | 9/1988 |
| EP | 0 312 852 | 4/1989 |
| EP | 0 417 928 | 8/1989 |
| EP | 0 417 928 B1 | 3/1991 |
| EP | 0 423 916 A1 | 4/1991 |
| EP | 0 483 372 A1 | 5/1992 |
| EP | 0 540 290 A2 | 5/1993 |
| EP | 0 729 767 A1 | 9/1996 |
| GB | 1205743 | 9/1970 |
| GB | 2 092 894 A | 8/1982 |
| GB | 2 135 585 A | 9/1984 |
| JP | 60-500520 | 4/1985 |
| JP | 61-41444 | 2/1986 |
| JP | 1-145076 | 7/1989 |
| RU | 660689 | 5/1979 |
| SU | 764684 | 9/1980 |
| SU | 1457921 | 2/1989 |
| WO | WO 83/03752 | 11/1983 |
| WO | WO 89/01798 | 3/1989 |

OTHER PUBLICATIONS

Palmaz J.C., et al., "Expandable Intrahepatic Portacaval Shunt Stents: Early Experience in the Dog," *AJR* 1985; 145: 821–825.

Palmaz J.C., et al., "Expandable Intrahepatic Portacaval Shunt Stents in Dogs with Chronic Portal Hypertension," *AJR* 1986; 147: 1251–1254.

Palmaz J.C., M.D., "Expandable Intraluminal Graft: A Preliminary Study," *Radiology* 1985; 156: 73–77.

Palmaz J.C., M.D., "Expandable intraluminal vascular graft: A feasibility study," *Surgery* 1986; 2: 199–205.

Frimberger E., "Expanding Spiral—A New Type of Prosthesis for the Palliative Treatment of Malignant Esophageal Stenoses," *Endoscopy* 1983; 15: 213–214.

Duprat G., Jr., M.D., et al., "Flexible Balloon–expanded Sten for Small Vessels," *Radiology* 1987; 162: 276–278.

Rosch J., M.D., et al., "Gianturco Expandable Wire Stents in the Treatment of Superior Vena Cava Syndrome Recurring After Maximum–Tolerance Radiation," *Cancer* 1987; 60:1243–1246.

Mullins C.E., M.D., et al., "Implantation of balloon–expandable intravascular grafts by cathertization in pulmonary arteries and systemic veins," *Circulation* 1988; 77: 188–199.

Papanicolaou N., et al., "Insertion of a Biliary Endoprosthesis Using a Balloon Dilation Catheter," *Gastrointestinal Radiology* 1985; 10: 394–396.

Sigwart U., M.D., et al., "Intravascular Stents To Prevent Occlusion And Restenosis After Transluminal Angioplasty," *The New England Journal of Medicine* 1987; 316: 701–706.

Rosch J., et al., "Modified Gianturco Expandable Wire Stents In Experimental and Clinical Use," *CIRSE* 1987; 31: 100–103.

Uchida B.T., et al., "Modifications of Gianturco Expandable Wire Stents," *AJR* 1988; 150: 1185–1187.

Cragg A., M.D., et al., "Nonsurgical Placement of Arterial Endoprostheses: A New Technique Using Nitinol Wire," *Radiology* 1983; 147: 261–263.

Palmaz J.C., M.D., et al., "Normal and Stenotic Renal Arteries: Experimental Balloon–expandable Intraluminal Stenting," *Radiology* 1987; Sep. 164 : 705–708.

Maass D., et al., "Radiological Follow–up of Transluminally Inserted Vascular Endoprostheses: An Experimental Study Using Expanding Spirals," *Radiology* 1984; 152: 659–663.

Rousseau H., M.D., et al., "Self–expanding Endovascular Prosthesis: An Experimental Study," *Radiology* 1987; Sep. 164: 709–714.

Duprat G. Jr., M.D., et al., "Self–expanding Metallic Stents for Small Vessels: An Experimental Evaluation," *Radiology* 1987; 162: 469–472.

Roland M., M.D., "Spiral Teflon Stent for Tuboplasty Involving Fimbria," *Obstetrics Gynecology* 1970; 36: 359–362.

Charnsangavej C., M.D., et al., "Stenosis of the Vena Cava: Preliminary Assessment of Treatment with Expandable Metallic Stents," *Radiology* 1986; Nov. 161: 295–298.

Wallace M.J., et al., "Tracheobronchial Tree: Expandable Metallic Stents Used in Experimental and Clinical Applications," *Radiology* 1986; 158: 309–312.

Balko A., M.D., et al., "Transfemoral Placement of Intraluminal Polyurethane Prosthesis for Abdominal Aortic Aneurysm," *Journal of Surgical Research* 1986; 40: 305–309.

Dotter C.T., M.D., et al., "Transluminal Expandable Nitinol Coil Stent Grafting: Preliminary Report," *Radiology* 1983; 147: 259–260.

Strecker E.P., et al., "A New Vascular Balloon–expandable Prosthesis—Experimental Studies and First Clinical Results," *Journal of Interventional Radiology* 1988; 3: 59–62.

Dorros G., et al., "Clinical Research: Angioplasty," *Circulation Supplement* 1986; 74: 1448; II363.

Schatz R., et al., "Balloon Expandable Intracoronary Stents in Dogs," *Circulation Supplement* 1986; 74: 1824–II458.

Radiology $72^{nd}$ Scientific Assembly and Meeting Agenda. 1986. Chicago: Nov. 30–Dec. 5.

American Heart Association $61^{st}$ Scientific Sessions. Abstract Form. A New Percutaneous Expandable Stent.

De Palma VA, Baier, Ford JW, Gott VL, Furuse A, "Investigation of Three Surface Properties of Several Metals and their relation to Blood Compatibility," *J Biomed Mater Res Symp* 1972; 3: 37–75.

Palmaz JC, Tio FO, Schatz RA, Alvarado CR, Garcia O, "Early Endothelisation of Balloon–expandable Stents: Experimental Observations," *Journal of Interventional Radiology* 1988; 119–124.

Schatz, Richard, "A View of Vascular Stents," *Circulation* 1989; 79: 445–457.

Schatz, Richard, "Introduction to Intravascular Stents," *Cardiology Clinics* 1988; vol. 6 No. 3: 357–372.

Baier RE, Dutton RC, "Initial events in interaction of blood with a foreign surface." *J Biomed Mater Res Symp* 1969; 3: 191–206.

Palmaz, Julio C., "Balloon–Expandable Intravascular Stent," *AJR:* 150, Jun. 1988: 1263–1269.

Schatz, Richard A., Palmaz, Julio C., "Intravascular Stents for Angioplasty," *Cardio*, Dec. 1987: 27–31.

Rosch J., Putnam J., Uchida B., "Gianturco Expandable Stents In Experimental And Clinical Use," Diagnostic Angiography and Interventional, Radiology Course, Mar. 1987; Hand–Out: 121–124.

Yoshioka, T., Wright K.C., Wallace S., Lawrence D.D. Jr., Ginaturco C., "Self–Expanding Endovascular Graft: An Experimental Study in Dogs," *AJR,* vol. 151 Oct. 1988: 673–676.

Wright K.C. Ph.D., Wallace S. M.D., Charnsangavej C. M.D., Carrasco, C.H. M.D., Gianturco C. M.D., "Percutaneous Endovascular Stents: An Experimental Evaluation," *Radiology,* 1985; 156: 69–72.

Rosch et al., "Experimental Intrahepatic Portacaval Anastomosis: Use of Expandable Gianturco Stents," *Radiology,* 1987; 162: 481–485.

Lawrence, Jr. et al., "Percutaneous Endovascular Graft: Experimental Evaluation," *Radiology,* 1987; 163: 357–360.

Mirion, M.D. et al., "Percutaneously Placed Endovascular Grafts for Aortic Aneurysms: Feasibility Study," *Radiology,* 1989; 170: 1033–1037.

Alvarado, R., et al., "Evaluation of Polymer–coated Balloon–expandable Stents in Bile Ducts," 170 *Radiology,* No. 3, Part 2, 975–978 Easton, PA: The Radiological Society of North America (Mar. 1989).

Becker, G.J., et al., "Simultaneous Angioplasty and Intraluminal Grafting with the Palmaz Expandable Intraluminal Graft," 72nd Scientific Assembly and Annual Meeting of the Radiological Society of North America, Chicago (Nov./Dec. 1986).

Becker, G.J. et al., "Early Experience with the Palmaz Stent in Human Iliac Angioplasty," *Indiana Medicine,* 286–292 (Apr. 1989).

Campbell, C.D., et al., "Expanded Microporous Polytetrafluoroethylene as a Vascular Substitute: A Two Year Follow–up," 85 *Surgery,* No. 2, 177–183, St. Louis: C.V. Mosby Co. (Feb. 1979).

Carrasco, C.H., et al., "Expandable Biliary Endoprosthesis: An Experimental Study," 145 *AJR,* 1279–1281, Baltimore: American Roentgen Ray Society (Dec. 1985).

Castañeda–Zuñiga, W.R., ed., *Transluminal Angioplasty,* New York: Thieme–Stratton, .iii–207 (1983).

Charnsangavej, C., et al., "Endovascular Stent for Use in Aortic Dissection: An In Vitro Experiment," 157 *Radiology,* 323–324, Easton, PA: The Radiological Society of North America (1985).

Cimochowski, G., et al., "Greenfield Filter Versus Mobin–Uddin Umbrella," 79 *Journal of Thoracic and Cardiovascular Surgery,* No. 3, 358–365, St. Louis: C.V. Mosby Co. (Mar. 1980).

Coons, H., et al., "Large–Bore, Long Biliary Endoprostheses (Biliary Stents) for Improved Drainage," 148 *Radiology,* 89–94, Easton, PA: The Radiological Society of North America (Jul. 1983).

Cope, C., "Balloon Dilatation of Closed Mesocaval Shunts," 135 *AJR,* 989–993, Baltimore: American Roentgen Ray Society (Nov. 1980).

Cragg, A., et al., "A New Percutaneous Vena Cava Filter," 141 *AJR,* 601–604, Baltimore: American Roentgen Ray Society (Sep. 1983).

Cragg, A.H., et al., "Percunatenous Arterial Grafting," 150 *Radiology,* No. 1, 45–49, Easton, PA: The Radiological Society of North America (Jan. 1984).

Dalessandri, K.M., et al., "The Effect of Lumbar Sympathectomy on Postsynaptic Vascular Smooth Muscle Response in the Lower Limb in Dogs," 11 *Cardiovascular and Interventional Radiology*, 82–85, New York: Springer–Verlag (1988).

Denny, D., et al., "Percutaneous Kimray–Greenfield Filter Placement by Femoral Vein Puncture," 145 *AJR*, 827–829, Baltimore: American Roentgen Ray Society (Oct. 1985).

Deriu, G., et al., "The Rationale for Patch–Graft Angioplasty After Carotid Endarterectomy: Early and Long–Term Follow–Up," 15 *Stroke*, No. 6, 972–979, Dallas: American Heart Association (Nov. 1984).

Dichek, D.A., et al., "Seeding of Intravascular Stents with Genetically Engineered Endothelial Cells," 80 *Circulation* 1347–1353, Dallas: American Heart Association (1989).

Dorland's Illustrated Medical Dictionary, 26th ed., 1981, pp. 675 & 759, Philadelphia: W.B. Saunders (1981).

Dotter, C., "Interventional Radiology–Review of an Emerging Field," 16 *Seminars in Roentgenology* No. 1 (Jan. 1981).

Dotter, C., et al., "Transluminal Treatment of Arteriosclerotic Obstruction," 30 *Circulation*, 654–670, Dallas: American Heart Association (Nov. 1964).

Edwards, W.S., "Arterial Grafts," 113 *Archives of Surgery*, No. 9, 1225–1233, Chicago: AMA (Nov. 1978).

Eichelter, P., et al., "Prophylaxis of Pulmonary Embolism," 97 *Archives of Surgery*, 348–356, Chicago: AMA (Aug. 1968).

Fogarty, T.J., et al., "Adjunctive Intraoperative Arterial Dilation: Simplified Instrumentation Technique," 116 *Archives of Surgery*, 1391–1398, Chicago: AMA (1981).

Fogarty, T.J., et al., "Current Status of Dilatation Catheters and Guiding Systems," 53 *The American Journal of Cardiology*, No. 12, 97C–100C, New York:Robert T. Brawn (Jun. 1984).

Fogarty, T.J., et al., "Intraoperative Coronary Artery Balloon–Catheter Dilation," 107 *American Heart Journal*, No. 4, 845–851, St. Louis, C.V. Mosby (1984).

Gardner, R.J., et al., "The Surgical Experience and a One to Sixteen Year Follow–Up of 277 Abdominal Aortic Aneurysms," 135 *American Journal of Surgery*, No. 1, 226–230 (Jan. 1978).

Goldstein, H., et al., "Transcatheter Occlusion of Abdominal Tumors," 120 *Radiology*, No. 3, 539–545, Easton, PA: Radiological Society of North America (Sep. 1976).

Greenfield, L., et al., "A New Intracaval Filter Permitting Continued Flow and Resolution of Emboli," 73 *Surgery*, No. 4, 599–606, St. Louis: C.V. Mosby (Apr. 1973).

Günther, R. et al., "Vena Caval Filter to Prevent Pulmonary Embolism: Experimental Study," 156 *Radiology*, No. 2, 315–320, Easton, PA: Radiological Society of North America Aug. 1985).

Harries–Jones, E.P., et al., "Repositioning of Biliary Endoprosthesis with Grüntzig Balloon Catheters," 138 *AJR*, 771–772, Baltimore: American Roentgen Ray Society (Apr. 1982).

Hoevels, J., et al., "Percutaneous Transhepatic Insertion of a Permanent Endoprosthesis on Obstructive Lesions of the Extrahepatic Bile Ducts," 4 *Gastrointestinal Radiology*, 367–377, New York: Springer–Verlag (1979).

Honickman, S., et al., "Malpositioned Biliary Endoprosthesis," 144 *Radiology*, 423–425, Easton, PA: Radiological Society of North America (Jul. 1982).

Hunter, J. et al., "Experimental Balloon Obstruction of the Inferior Vena Cava," 171 *Annals of Surgery*, No. 2, 315–320, J.B. Lippincott (Feb. 1970).

Inoue, K., et al., "Clinical Application of Transvenous Mitral Commissurotomy by a New Balloon Catheter," 87 *J. Thorac. Cardiovascular Surg.*, No. 3, 394–402, St. Louis: C.V. Mosby (Mar. 1984).

Kan, J.S., et al., "Percutaneous Balloon Valvuloplasty: A New Method for Treating Congenital Pulmonary—Valve Stenosis," 307 *N. Engl. J. Med.*, No. 9, 540–542, Boston: Massachusetts Medical Society (1982).

Kerlan, Jr., et al., "Biliary Endoprostheses: Insertion Using a Combined Peroral–Transhepatic Method," 150 *Radiology*, No. 3, 828–830, Easton, PA: Radiological Society of North America (1984).

Kerlan, R.K., Jr., et al., "A Simple Method for Insertion of Large Untapered Catheters," 141 *AJR*, 792, Baltimore: American Roentgen Ray Society (Oct. 1983).

Lababidi, Z. et al., "Percuntatenous Balloon Aortic Valvuloplasty: Results in 23 Patients," 53 *Am. J. Cardiol*, 194–197, Robert T. Brawn (Jan. 1984).

Lary, B., et al., "The Experimental Use of Steel Mesh Tubes for the Replacement of Arterial Segments", 72 *AMA Archives of Surgery*, 69–75, Chicago: AMA (Jan. 1956).

Lewandowski, B., et al., "The Air–Filled Hepatic Duct: The Saber Sign as an Aid to the Radiographic Diagnosis Pneumobilia," 153 *Radiology*, No. 2, 329–332, Easton, PA: Radiological Society of North America (Nov. 1984).

Lund, G., et al., "A New Vena Caval Filter for Percutaneous Placement and Retrieval: Experimental Study," 152 *Radiology*, No. 2, 369–372, Easton, PA: Radiological Society of North America (Aug. 1984).

Lunderquist, A., et al., "Guidewire for Percutaneous Transhepatic Cholangiography," 132 *Radiology*, No. 1, 228, Easton, PA: Radiological Society of North America (Jul. 1979).

Güther, R. M.D., et al., "Percutaneous Nephropyelostomy Using a Fine–Needle Puncture Set," 132 *Radiology*, No. 1, 228–230, Easton, PA: Radiological Society of North America (Jul. 1979).

Mobin–Uddin, K., et al., "Caval Interruption for Prevention of Pulmonary Embolism" 99 *Archives on Surgery*, 711–715, Chicago: AMA (Dec. 1969).

Mobin–Uddin, K., et al., "The Inferior Vena Cava Umbrella Filter," 17 *Progress in Cardiovascular Diseases*, No. 5, 391–399, Crune & Stratton (Mar./Apr. 1975).

Nanda, R., et al., "Effect of Maxillary Osteotomy on Subsequent Craniofacial Growth in Adolescent Monkeys," *Am J Orthod* (May 1983).

Natiella, J.R., et al., "Tissue Response to Surface–Treated Tantalum Implants: Preliminary Observations in Primates," 13 *J. Biomed Mater Res.*, No. 4, 631–643 (Jul. 1979)

Palestrant, A., et al., "Comparative In Vitro Evaluation of the Nitinol Inferior Vena Cava Filter," 145 *Radiology*, 351–355, Easton, PA: Radiological Society of North America (Nov. 1982).

Dr. Julio Palmaz's Monograph (1980).

Palmaz, J., et al., "Removable Biliary Endoprosthesis," 140 *AJR*, 812–814, Baltimore: American Roentgen Ray Society (Apr. 1983).

Dr. Julio Palmaz's Monography (May 18, 1983).

Palmaz, J., et al., "Experimental Balloon Expandable Intraluminal Stenting of Normal and Abnormal Renal Arteries," 72nd RSNA Meeting, Chicago, Illinois, pp. 1–23 [plus figures] (Nov. 1986).

Palmaz, J., et al., "Balloon Expandable Intraluminal Grafting of Normal and Abnormal Renal Arteries: Experimental Study," 72nd Scientific Assembly and Annual Meeting, Radiological Society of North America, Chicago (Nov./Dec. 1986).

Palmaz, J., et al., "Balloon Expandable Intra–Arterial Stents: Effect of Anticoagulation on Thrombus Formation," 76 *Circulation Supplement,* Part II, No. 4, 0180, Dallas: American Heart Association (Oct. 1987).

Palmaz, J., et al., "Intraluminal Stents in Atherosclerotic Iliac Artery Stenosis: Preliminary Report of a Multicenter Study," 168 *Radiology,* No. 3, 727–731, Easton, PA: Radiological Society of North America (Sep. 1988).

Palmaz, J., et al., "Balloon–Expandable Intraarterial Stents: Effect of Antithrombotic Medication on Thrombus Formation," *Pros and Cons in PTA and Auxiliary Methods,* 170–178 (1989).

Palmaz, J. "Chapter 30: Overview of Intravascular Stents," in Ducksoo Kim and Dan E. Orron, *Perhipheral Vascular Imaging and Intervention,* St. Louis: Mosby Year Book, 507–508, (A. Patterson ed. 1992).

Pate, J. ,et al., "A New Form of Vena Caval Interruption," 169 *Annals of Surgery,* No. 6, 873–880, J.B. Lippincott (Jun. 1969).

Puel, J., et al., "Intravascular Stents to Prevent Restenosis After Transluminal Coronary Angioplasty," 76 *Circulation Supplement,* Part II, No. 4, 0105, Dallas: American Heart Association (Oct. 1987).

Rashkind, W.J., et al., "Creation of an Atrial Septal Defect Without Thoracotomy: A Palliative Approach to Complete Transposition of the Great Arteries," 196 *JAMA,* No. 11, 173–174, Chicago: AMA (Apr.–Jun. 1966).

Rees, C.R., et al., "The Hemodynamic Effects of the Administration of Ionic and Nonionic Contrast Materials into the Pulmonary Arteries of a Canine Model of Acute Pulmonary Hypertension," 23 *Investigative Radiology,* No. 3, 184–189 (Mar. 1988).

Rees, C.R., et al., "DSA in Acute Gastrointestinal Hemorrhage: Clinical and in Vitro Studies," 169 *Radiology,* No. 2, 499–503, Easton, PA: Radiological Society of North America (Nov. 1988).

Rees, C.R., et al., "Angioplasty and Stenting of Completely Occluded Iliac Arteries," 172 *Radiology,* No. 3, Part. 2, 953–959, Easton, PA: Radiological Society of North America (Sep. 1989).

Richter, G.M., et al., "Der Transjuguslaere Intrahepatische Portosystemische Stent–Shunt (TIPSS); Eine Neue Nichtoperative, Perkutane Methode," 29 *Radiologe,* 406–411, Springer–Verlag (1989) [Article includes an English Summary].

Richter, G.M. et al., "Die Behandlung eines akuten Beckenarterienverschlusses durch Katheterlyse, Katheterdilatation und Implantation einer neuartigen metallischen Gefäßendoprothese," 60 *Der Chirurg,* No. 5, 346–351, Berlin: Springer–Verlag (May 1989) [Article includes an English Summary].

Ring, E.J., et al., "A Simple, Indwelling Biliary Endoprosthesis Made From Common Available Catheter Material," 139 *AJR,* 615–617, Baltimore: American Roentgen Ray Society (Sep. 1982).

Roehm, Jr., et al., "Percutaneous Transcatheter Filter for the Interior Vena Cava," 150 *Radiology,* No. 1, 255–257, Easton, PA: Radiological Society of North America (Jan. 1984).

Rollins, N., et al., "Self–Expanding Metallic Stents: Preliminary Evaluation in an Atheroschlerotic Model," 163 *Radiology,* No. 3, 739–742, Easton, PA: Radiological Society of North America (Jun. 1987).

Rosch, J., et al., "Transjugular–Intrahepatic Portacaval Shunt: An Experimental Work," 121 *The American Journal of Surgery,* 588–592, New York: Reuben H. Donnelley (May 1971).

Rousseau, H., et al., "Percutaneous Vascular Stent: Experimental Studies and Preliminary Clinical Results in peripheral Arterial Diseases," *Inter. Angio.* 6, 153–161 (1987).

Schatz, R., et al., "Balloon Expandable Intravascular Grafts," 16th Annual Symposium of the Texas Health Institute—International Symposium on Interventional Cardiology, Houston (Sep. 1986).

Schatz, R., et al., "Balloon Expandable Intracoronary Stents in the Adult Dog," 59th Scientific Sessions of the American Heart Association Meeting, Dallas (Nov. 1986).

Schatz, R., et al., "Balloon Expandable Intracoronary Stents in the Adult Dog," 76 *Circulation* No. 2, 450–457, Dallas: American Heart Association (Aug. 1987).

Schatz, R., et al., "New Technology in Angioplasty: Balloon–Expandable Intravascular Stents," 2 *New Developments in Medicine,* No. 2, 59–75 (Sep. 1987).

Semb, B.K.H., et al., "Balloon Valvulotomy of Congenital Pulmonary Valve Stenosis with Tricuspid Valve Insufficiency," 2 *Cardiovascular Radiology,* 239–241, New York: Springer–Verlag (1979).

Sigwart, U., et al., "One Year of Percutaneous Coronary Stenting," 76 *Circulation Supplement,* Part II, No. 4, 0104, Dallas: American Heart Association (Oct. 1987).

Sigwart, U., et al., "Intial Experience With A New Approach to Stenting of Peripheral and Coronary Arteries," (date unknown).

Simon, M., et al., "A Vena Cava Filter Using Thermal Shape Memory Alloy," 125 *Radiology,* 89–94, Easton, PA: Radiological Society of North America (Oct. 1977).

Smith, D., et al., Safe and Effective Catheter Angiography Through Prosthetic Vascular Grafts, 138 *Radiology,* No. 2, 487–488, Easton, PA: Radiological Socity of North America (Feb. 1981).

Solberg, S., et al., "Cold Induced Endothelial Cell Detachment in Human Saphenous Vein Grafts," 28 *Journal of Cardiovascular Surgery,* No. 5, 571–575, Minerva Medica (Sep.–Oct. 1987).

Stack, R., M.D., "A New Highly Flexible Balloon–Expandable Endovasular Stent: Initial Experiential Results and Up To Six Months Follow–up," Laser One Meeting, Newport Beach, California (May 11–13, 1989).

Strecker, E.P., et al., "Perkutan Implantierbare, Durth Balloon Aufdehnbare Gefäßprothese," 113 *Dtsch Med Wschr,* No. 14, 538–542, Stuttgart: Georg Thieme Verlag (1988) [Article includes an English Summary].

Teplick, S.K., et al., "A New Biliary Endoprosthesis," 141 *AJR,* 799–801, Baltimore: American Roentgen Ray Society (Oct. 1983).

Trent, M., M.D., et al., "An Expandable Intravascular Stent for the Maintenance of Luminal Patency," Division of Vascular Surgery and the Department of Surgery, Newark Beth Israel Medical Center, date unknown.

9 *Journal of the American College of Cardiology* 2(Supplement A): 106A, (from Abstracts of the 36$^{th}$ Annual Scientific Session, American College of Cardiology, New Orleans, Louisiana Mar. 8–12, 1987), Elsevier (Feb. 1987).

Plaintiff Advanced Cardiovascular System's Answering Brief in Opposition to Defendant's Motion to Disqualify Lead Trial Counsel, Advanced Cardiovascular Systems, Inc. v. Arterial Vascular Engineering, Inc., C.A. No. 98–314–SLR (D. Del. Brief dated Sep. 18, 1998) (includes Exhibits A–W).

Answer and Counterclaim of Advanced Cardiovascular Systems, Inc. and Guidant Sales Corporation to Amended and Supplemental Complaint of Medtronic AVE, Inc. and Medtronic USA, Inc., Medtronic AVE, Inc. et al. v. Advanced Cardiovascular Systems, Inc., et al., C.A. No. 98–80–SLR (D. Del., Answer and Counterclaim dated Nov. 9, 2000).

Answer to Second Amended Complaint, Affirmative Defenses and Conterclaims, Medtronic AVE, Inc. et al. v. Boston Scientific Corp., et al., C.A. No. 98–478–SRL (D. Del. Answer dated Jul. 13, 2000).

First Amended Complaint Asserting Derivative and Individual Causes of Action for Breach of Contract; Breach of Covenant of Good Faith and Fair Dealing; Breach of Fiduciary Duty; Misappropriation of Trade Secrets; Unfair Competition; Intentional Misrepresentation; Concealment; Nondisclosure; Unjust Enrichment and Breach of Confidence, Rodolfo Di Massa, M.D., et al., v. Simon Stertzer, M.D., et al., No. 222363 (Cal. Super. Ct., Sonoma County, First Amended Complaint filed Feb. 1, 2000) (Includes Exhibit A).

Rodolfo Di Massa's Supplemental Answers to Defendant Medtronic Arterial Vascular Engineering Inc.'s First Set of Specially Prepared Interrogatories, Rodolfo Di Massa, M.D., et al., v. Simon Stertzer, M.D., et al., No. 222363 (Cal. Super. Ct., Sonoma County, Supplemental Answers dated Mar. 15, 2000).

Declaration of Paul Bonneau, Jr., Rodolfo Di Massa, M.D., et al. v. Simon Stertzer, M.D., et al., No. 222363 (Cal. Super Ct., Sonoma County, Declaration dated May 12, 2000) (including Exhibits D1–D3).

Plaintiff's Eight Amended Petition, Azam Anwar, M.D., et al. v. Arterial Vascular Engineering, Inc., No. 96–05323–M (Tex. Dist. Ct., Dallas County, 298$^{th}$ Judicial Dist., Petition dated Oct. 28, 1998).

Urteil [Judgment], Inflow Dynamics AG, et al. v. Arterial Vascular Engineering, Inc., Nos. 4 Ni 33/99 (EU) verb. [joined with ] 4 Ni 41/99 (EU) (Bundespatentgerricht [BPatG] [Federal Court for Patent Matters] Sep. 5, 2000) [English Translation included].

* cited by examiner

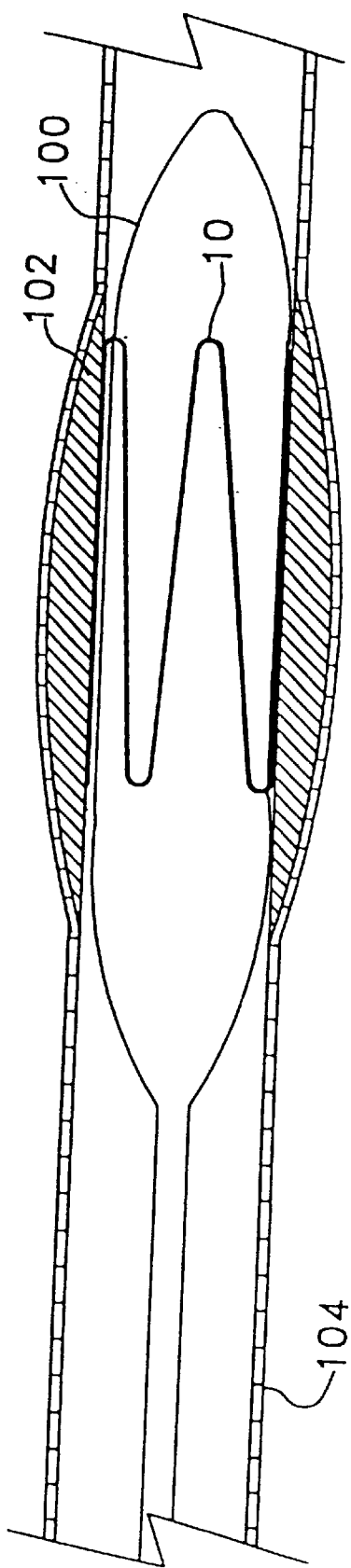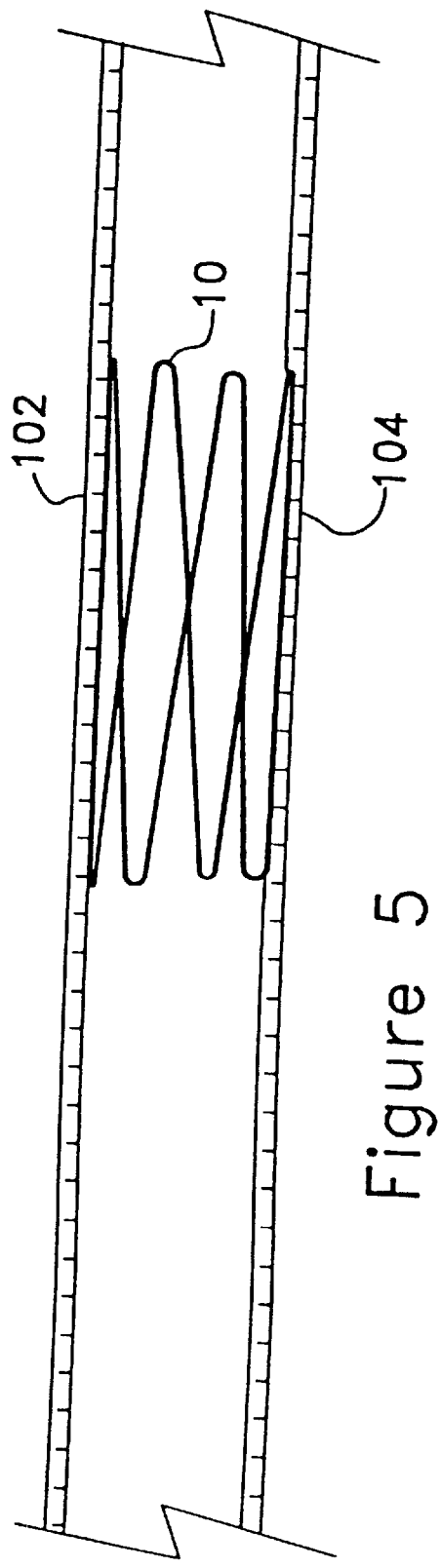
Figure 4
Figure 5

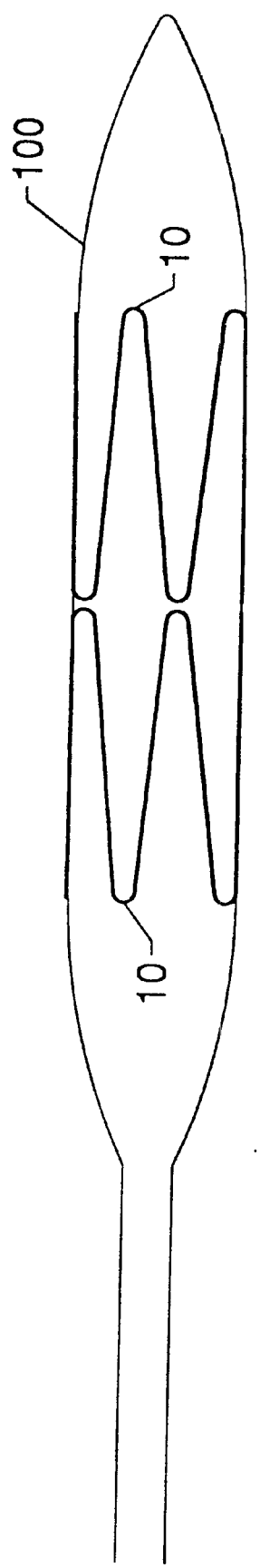

ENDOVASCULAR SUPPORT DEVICE AND METHOD

This application is a continuation of application Ser. No. 08/471,738, filed Jun. 6, 1995, now U.S. Pat. No. 5,891,140, which is a divisional of Ser. No. 08/172,420, filed on Dec. 22, 1993, now abandoned, which is a division of application Ser. No. 07/398,180, filed Aug. 24, 1989, now U.S. Pat. No. 5,292,331.

FIELD OF THE INVENTION

The present invention relates generally to medical devices and particularly relates to implantable devices for treating narrowing of coronary or peripheral vessels in humans.

BACKGROUND OF THE INVENTION

Cardiovascular disease, including atherosclerosis, is the leading cause of death in the U.S. The medical community has developed a number of methods for treating coronary heart disease, some of which are specifically designed to treat the complications resulting from atherosclerosis and other forms of coronary arterial narrowing.

The most impelling development in the past decade for treating atherosclerosis and other forms of coronary narrowing is percutaneous transluminal coronary angioplasty, hereinafter referred to simply as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions and is related to the nature of the plaque. Soft, fatty plaque deposits are flattened by the balloon and hardened deposits are cracked and split to enlarge the lumen. The wall of the artery itself is also stretched when the balloon is inflated.

PTCA is performed as follows: A thin-walled, hollow guiding catheter is typically introduced into the body via a relatively large vessel, such as the femoral artery in the groin area or the brachial artery in the arm. Access to the femoral artery is achieved by introducing a large bore needle directly into the femoral artery, a procedure known as the Seldinger Technique. Once access to the femoral artery is achieved, a short hollow sheath is inserted to maintain a passageway during PTCA. The flexible guiding catheter, which is typically polymer coated, and lined with Teflon, is inserted through the sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired.

After the guiding catheter is advanced to the ostium of the coronary artery to be treated by PTCA, a flexible guidewire is inserted into the guiding catheter through a balloon and advanced to the area to be treated. The guidewire provides the necessary steerability for lesion passage. The guidewire is advanced across the lesion, or "Wires" the lesion, in preparation for the advancement of a polyethylene, polyvinyl chloride, polyolefin, or other suitable substance balloon catheter across the guide wire. The balloon, or dilatation, catheter is placed into position by sliding it along the guide wire. The use of the relatively rigid guide wire is necessary to advance the catheter through the narrowed lumen of the artery and to direct the balloon, which is typically quite flexible, across the lesion. Radiopaque markers in the balloon segment of the catheter facilitate positioning across the lesion. The balloon catheter is then inflated with contrast material to permit fluoroscopic viewing during treatment. The balloon is alternately inflated and deflated until the lumen or the artery is satisfactorily enlarged.

Unfortunately, while the affected artery can be enlarged, in some instances the vessel restenoses chronically, or closes down acutely, negating the positive effects of the angioplasty procedure. In the past, such restenosis has frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such mechanical endoprosthetic devices, which are generally referred to as stents, are typically inserted into the vessel, positioned across the lesion, and then expanded to keep the passageway clear. Effectively, the stent overcomes the natural tendency of the vessel walls of some patients to close back down, thereby maintaining a more normal flow of blood through that vessel than would be possible if the stent were not in place.

Various types of stents have been proposed, although to date none has proven satisfactory. One proposed stent involves a tube of stainless wire braid. During insertion, the tube is positioned along a delivery device, such as a catheter, in extended form, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise. For example, one such stent is a self-expanding stainless steel wire braid. Other forms of stents include various types tubular metallic cylinders expanded by balloon dilatation. One such device is referred to as the Palmaz stent, discussed further below.

Another form of stent is a heat expandable device. This device, originally designed using NITINOL by Dotter has recently been modified to a new tin-coated, heat expandable coil by Regan. The stent is delivered to the affected area on a catheter capable of receiving heated fluids. Once properly positioned, heated saline is passed through the portion of the catheter on which the stent is located, causing the stent to expand. Numerous difficulties have been encountered with this device, including difficulty in obtaining reliable expansion, and difficulties in maintaining the stent in its expanded state.

Perhaps the most popular stent presently under investigation in the United States is referred to as the Palmaz stent. The Palmaz stent involves what may be thought of as a stainless steel cylinder having a number of slits in its circumference, resulting in a mesh when expanded. The stainless steel cylinder is delivered to the affected area by means of a balloon catheter, and is then expanded to the proper size by inflating the balloon.

Significant difficulties have been encountered with all prior art stents. Each has its percentage of thrombosis, restenosis and tissue in-growth, as well as varying degrees of difficulty in deployment. Another difficulty with at least come of prior art stents is that they do not readily conform to the vessel shape. In addition, the relatively long length of such prior art stents has made it difficult to treat cursed vessels, and has also effectively prevented successful implantation of multiple such stents. Anticoagulants have historically been required at least for the first three months after placement. These and other complications have resulted in a low level of acceptance for such stents within the medical community, and to date stents have not been accepted as a practical method for treating chronic restenosis.

Thus there has been a long felt need for a stent which is effective to maintain a vessel open, without resulting in significant thrombosis, which may be easily delivered to the affected area, easily expanded to the desired size, easily conformed to the affected vessel, and easily used in multiples to treat curved vessels and varying lengths of lesions.

SUMMARY OF THE INVENTION

The present invention substantially reduces the complications and overcomes the limitations of the prior art devices. The endovascular support device of the present invention comprises a device having very low mass which is capable of being delivered to the affected area by means of a slightly modified conventional balloon catheter similar to that used in a standard balloon angioplasty procedure The support device of the present invention may then be expanded by normal expansion of the balloon catheter used to deliver the stent to the affected area, and its size can be adjusted within a relatively broad range in accordance with the diagnosis of the treating physician.

Because of the range of diameters through which the support device of the present invention may be expanded, it may be custom expanded to the specific lesion diameter, and is readily conformable to the vessel shape. In addition, a plurality of support devices of the present invention may be readily implanted in a number commensurate with the length of the lesion under treatment. As a result, curved or "S" shaped vessels may be treated.

The stent, or endovascular support device, of the present invention may preferably be comprised of implantable quality high grade stainless steel, machined specially for intravascular applications. The support device may comprise, in effects, a metal circle or ellipsoid formed to create a plurality of axial bends, thereby permitting compression of the stent onto a delivery catheter, and subsequent expansion once in place at the affected area.

It is one object of the present invention to provide a stent which substantially overcomes the limitations of the prior art.

It is a further object of the present invention to provide a stent capable of being implanted simply and reliably.

Another object of the present invention is to provide a stent which does not result in significant thrombosis at the point of implant.

Yet another object of the present invention is to provide a stent which can be selectively sized in accordance with the anatomic configuration dictated by the lesion itself.

A still further object of the present invention is to provide a method for supplying an endovascular support device which permits a plurality of such devices to be implanted commensurate with the length of the lesion under treatment.

These and other objects of the present invention can be better appreciated from the following detailed description of the invention, taken in conjunction with the attached drawings.

FIGURES

FIG. 4 shows a support device according to the present invention in its expanded form within a sectioned portion of a vessel including a lesion.

FIG. 5 shows a support device of the present invention in its expanded form within a sectioned portion of a lesion after removal of the balloon catheter.

Figure 6A:
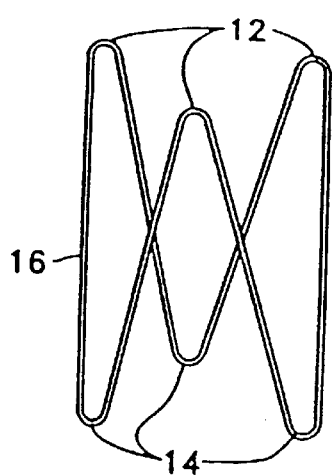
Figure 6B:
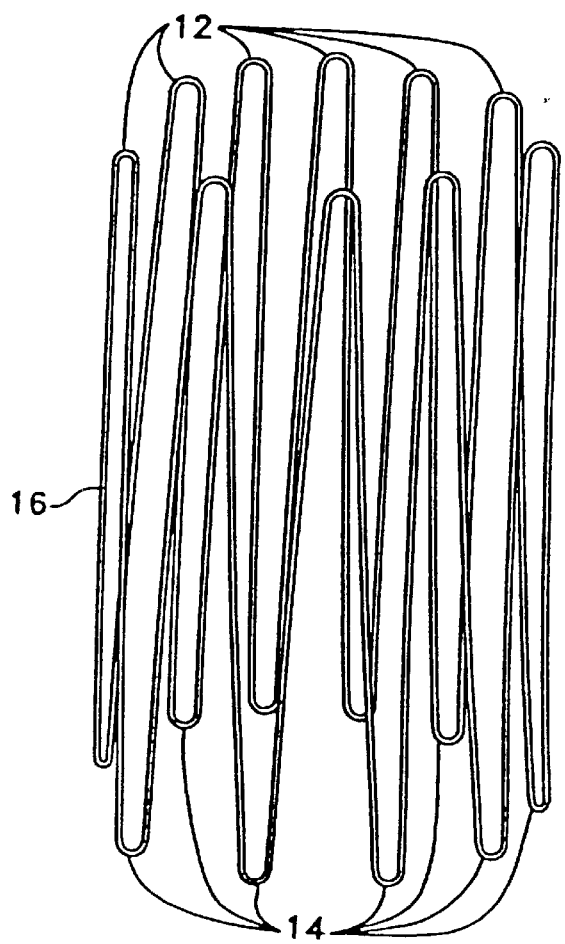

FIGS. 6a–b show alternative configurations of a support device according to the present invention.

FIG. 7 shows an alternate configuration of a support device constructed according to the present invention and compressed into a balloon catheter.

DETAILED DESCRIPTION OF THE INVENTION

Figure 1:
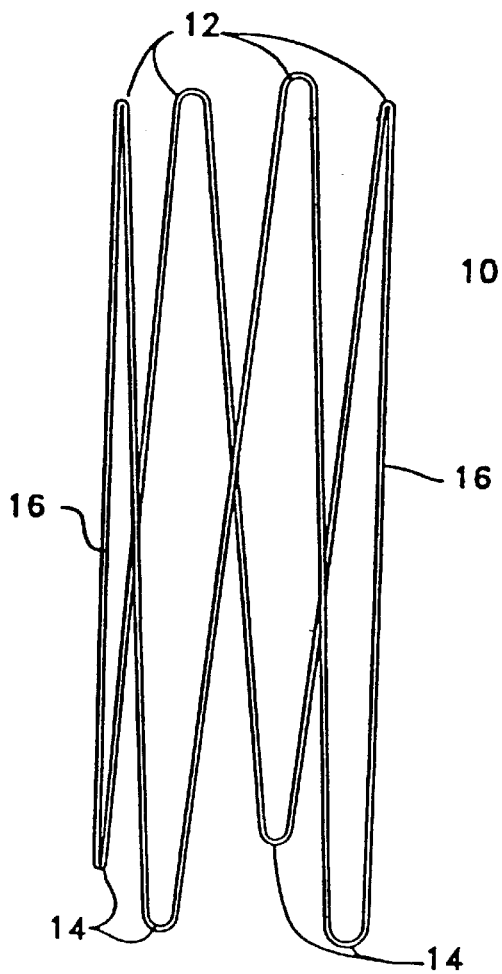
FIG. 1 shows a perspective view of an endovascular support device constructed according to the present invention, in its expanded form.

Referring first to FIG. 1, an endovascular support device 10, referred to hereinafter more conveniently as a stent, constructed in accordance with the present invention can be seen in perspective view. The stent 10 of FIG. 1 is shown in its expanded form, prior to compression over a suitable delivery system as discussed in detail hereinafter.

In a preferred embodiment, the stent 10 comprises a single piece of material, bent to form a plurality of upper axial turns 12 and lower axial turns 14. In the embodiment shown in FIG. 1, four upper turns 12 are connected to the four lower turns 14 by substantially straight segments 16. The axial turns 12 and 14 can be seen to permit the stent 10 to be compressed or expanded over a wide range while still maintaining significant mechanical force, such as required to prevent a vessel from restenosing, While a preferred embodiment comprises a single piece of material, in some instances a suitably welded wire may be acceptable.

It will be appreciated that the number of turns 12 and 14 can vary over a reasonably wide range and may in fact vary between two and ten such turns or peaks. However, it is currently believed that the optimum number of turns or peaks will range between three and five for most applications, and particularly for cardiovascular applications.

The stent 10 is preferably constructed of implantable materials having good mechanical strength. An embodiment which has proven successful in preliminary testing is machined from 316LSS implantable quality stainless steel bar stock. The bar stock is machined to form substantially a toroid, which is then acid etched in phosphoric and sulfuric acid at approximately 180° to 185° to break the edges. The etched toroid is then plated with copper to avoid galling and to provide lubricity.

The copper plated toroid is then bent to the shape of the stent 10 shown in FIG. 1, after which the copper plating is stripped from the stent. The stent is then returned to the acid bath to reduce the wire size to the desired diameter, which is in the range of 0.002" to 0.025". It is presently believed that the optimum wire size for the final product is in the range of 0.008" to 0.009". It will be appreciated that the strength of the stent—that is, its ability to prevent restenosis—is inversely proportional to the number of peaks or turns in the stent, so that stents having a greater number of turns will typically be formed of larger wire diameters. Finally, although not required in all cases, the outside of the stent may be selectively plated with platinum to provide improved visibility during fluoroscopy. The cross-sectional shape of the finished stent may be circular, ellipsoidal, rectangular, hexagonal, square, or other polygon, although at present it is believed that circular or ellipsoidal may be preferable.

The minimum length of the stent, or the distance between the upper turns 12 and lower turns 14, is determined in large measure by the size of the vessel into which the stent will be implanted. The stent 10 will preferably be of sufficient length as to maintain its axial orientation within the vessel without shifting under the hydraulics of blood flow (or other fluid flow in different types of vessels), while also being long enough to extend across at least a significant portion of the affected area. At the same time, the stent should be short enough as to not introduce unnecessarily large amounts of material as might cause undue thrombosis. Typical cardiovascular vessels into which the stent 10 might be implanted range from 1.5 millimeters to five millimeters in diameter, and corresponding stents may range from one millimeter to two centimeters in length. However, in most instances the stent will range in length between 3.5 millimeters and 6 millimeters. Preliminary testing of stents having a length between 3.5 millimeters and 4.5 millimeters has been performed with good success outside the United States, and testing on animals is also ongoing.

Figure 2:
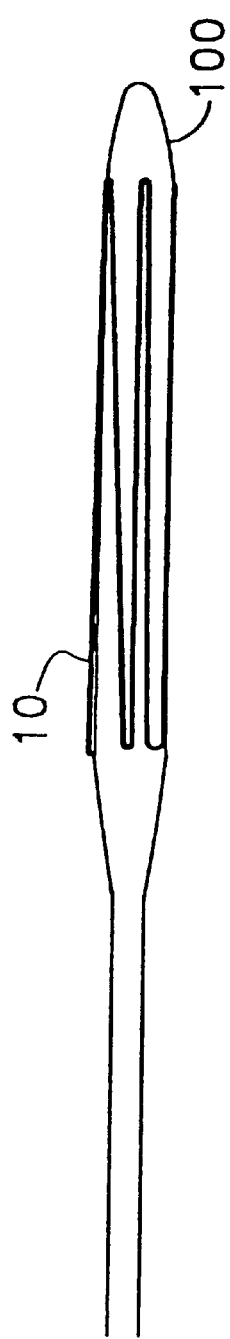
FIG. 2 shows a support device constructed according to the present invention and compressed onto a balloon catheter.

Once the wire size of the stent 10 has been reduced to the desired size, the stent 10 may be crimped onto a balloon 100, as shown in FIG. 2, for delivery to the affected region 102 of a vessel 104 such as a coronary artery. For the sake of simplicity, the multiple layers of the vessel wall 104 are shown as a single layer, although it will be understood by those skilled in the art that the lesion typically is a plaque deposit within the intima of the vessel 104.

One suitable balloon for delivery of the stent 10 is manufactured by Advanced Cardiovascular Systems, Inc., of Santa Clara, Calif. ("ACS"), and is eight millimeters in length with Microglide on the shaft only. The stent-carrying balloon 100 is then advanced to the affected area and across the lesion 102 in a conventional manner, such as by use of a guide wire and a guide catheter (not shown). A suitable guide wire is the 0.014" Hi Torque Floppy manufactured by ACS, and a suitable guiding catheter is the ET0.076 lumen guide catheter, also manufactured by ACS.

Figure 3:
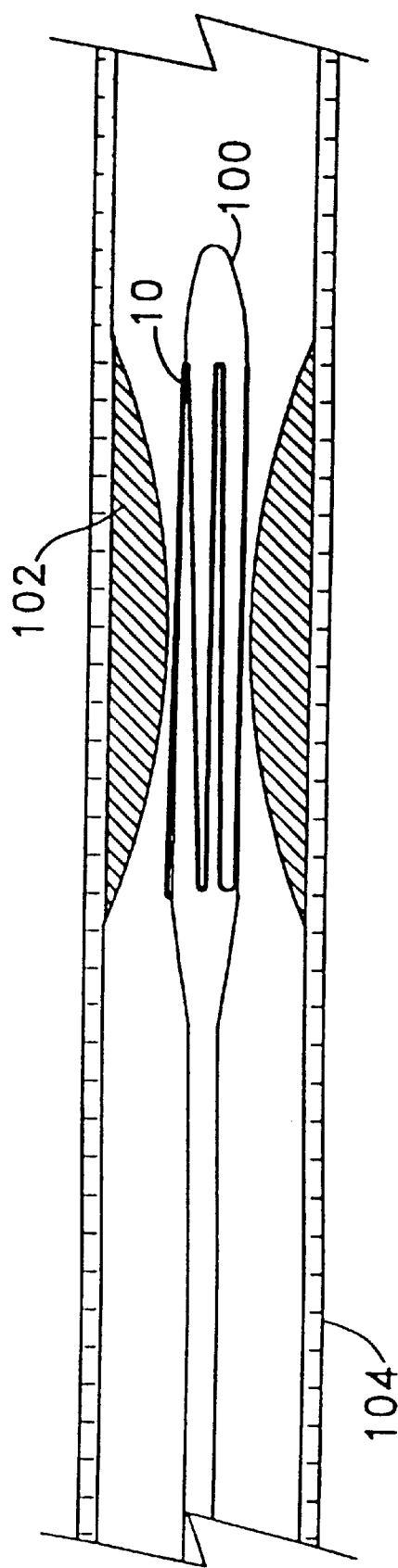
FIG. 3 shows a support device compressed onto a balloon catheter as shown in FIG. 2 and positioned within a sectioned portion of an affected area of a anery of other vessel.

Once the balloon 100 is in place across the lesion 102, as shown in FIG. 3, the balloon 100 may be inflated, again substantially in a conventional manner. In selecting a balloon, it is helpful to ensure that the balloon will provide radially uniform inflation so that the stent 10 will expand equally along each of the peaks. The inflation of the balloon 100, shown in FIG. 4, causes the expansion of the stent 10 from its crimped configuration back to a shape substantially like that shown in FIG. 1. The amount of inflation, and commensurate amount of expansion of the stent 10, may be varied as dictated by the lesion itself, making the stent of the present invention particularly flexible in the treatment of chronic restenosis.

Because of the inflation of the balloon, the lesion 102 in the vessel 104 is expanded, and causes the arterial wall of the vessel 104 to bulge radially, as simplistically depicted in FIG. 4. At the same time, the plaque deposited within the intima of the vessel is displaced and thinned, and the stent 10 is embedded in the plaque or other fibrotic material adhering to the intima of the vessel 104.

Following inflation of the balloon 100 and expansion of the stent 10 within the vessel 104, the balloon is deflated and removed. The exterior wall of the vessel 104 returns to its original shape through elastic recoil. The stent 10, however, remains in its expanded form within the vessel, and prevents further restenosis of the vessel. The stent maintains an open passageway through the vessel, as shown in FIG. 4, so long as the tendency toward restenosis is not greater than the mechanical strength of the stent 10. Because of the low mass of the support device 10 of the present invention, thrombosis is less likely to occur. Ideally, the displacement of the plaque deposits and the implantation of the stent 10 will result in a smooth inside diameter of the vessel 104, although this ideal cannot be achieved in all cases.

One of the advantages of the stent 10 is that multiple stents may be used in the treatment of a single lesion. Thus, for example, in the event the affected area shown in FIGS. 3 and 4 was longer than the stent 10, additional stents 10 could be positioned elsewhere along the lesion to prevent restenosis. In preliminary testing, up to four stents have been used successfully along a single lesion. Due to the conformablity of the stent 10, not only can varying lesion lengths be treated, but curved vessels and "S" shaped vessels may also be treated by the present invention. In instances where it is known in advance that multiple stents will be the preferred method of treatment, a plurality of such stents may be positioned along a single balloon catheter for simultaneous delivery to the affected area as shown in FIG. 7.

As discussed above, the number of peaks or turns 12 and 14 in the shent 10 may vary between two and ten. To this end, shown in FIGS. 6a and 6b are two alternative configurations of the stent 10. The alternative embodiment shown in 6a can be seen to have three upper and three lower peaks or turns, while the embodiment shown in FIG. 6b can be seen to have ten upper and ten lower peaks.

While the primary application for the stent 10 is presently believed to be treatment of cardiovascular disease such as atherosclerosis or other forms of coronary narrowing, the stent 10 of the present invention may also be used for treatment of narrowed vessels in the kidney, leg, carotid, or elsewhere in the body in such other vessels the size of the stent may need to be adjusted to compensate for the differing sizes of the vessel to be treated, bearing in mind the sizing guidelines provided above.

Having fully described a preferred embodiment of the invention, those skilled in the art will immediately appreciate, given the teachings herein, that numerous alternatives and equivalents exist which do not depart from the present invention. It is therefore to be understood that the present invention is not to be limited by the foregoing description, but only by the appended claims.

I claim:

1. A balloon-expandable stent comprising:
   a plurality of generally sinusoidally-shaped, plastically deformable rings capable of retaining a compressed configuration when mounted onto a balloon catheter and having a first diameter when mounted onto the balloon catheter;
   each ring comprising substantially straight segments oriented generally parallel to a longitudinal axis of its ring in its first diameter;
   each segment having a first end and a second end, with a first end of a first segment connected to a first end of a second segment by a first turn;
      a second end of the second segment connected to a second end of a third segment by a second turn;
      a first end of the third segment connected to a first end of a fourth segment by a third turn, and so on until a second end of an Nth segment is connected to a second end of the first segment by an Nth turn;
      wherein each segment is connected to another segment at its ends and at no point intermediate its ends; and
   wherein the rings are expandable to a second diameter larger than the first diameter.

2. The stent of claim 1, wherein the segments have a generally hexagonal cross-section.

3. The stent of claim 1, wherein the segments have a generally rectangular cross-section.

4. The stent of claim 1, wherein the segments have a generally round cross-section.

5. The stent of claim 1, wherein the rings are not connected to each other.

6. The stent of claim 1, wherein the rings are formed from a toroid.

7. The stent of claim 1, wherein the turns are curved.

8. A balloon-expandable stent for implantation within a vessel within the human body comprising:

a plurality of plastically deformable generally sinusoidally-shaped circular members; each circular member including a plurality of substantially straight segments, each segment having a first and second ends, wherein the first end of a first segment is connected to the first end of a second segment;

the second end of the second segment is connected to the second end of the third segment;

the first end of the third segment is connected to the first end of the fourth segment, and so on until the second end of a last segment is connected to the second end of the first segment, each circular member capable of retaining a compressed configuration while mounted onto an outer surface of a balloon catheter until application of a radial force to form an expanded configuration.

9. The stent of claim 8, wherein the segments have a generally hexagonal cross-section.

10. The stent of claim 8, wherein the segments have a generally rectangular cross-section.

11. The stent of claim 8, wherein the segments have a generally round cross-section.

12. The stent of claim 8, wherein the generally sinusoidally-shaped circular members are not connected to each other.

13. The stent of claim 8, wherein the generally sinusoidally-shaped circular members are formed from a toroid.

14. The stent of claim 8, wherein all segments are aligned in a generally same direction, when in a compressed configuration mounted on an outer surface of a balloon catheter.

15. The stent of claim 8, wherein all segments are aligned generally parallel to a longitudinal axis of the stent, when in a compressed configuration mounted on an outer surface of a balloon catheter.

16. A balloon-expandable stent comprising:

a plurality of adjacent and non-overlapping, generally circular members, each circular member including a plurality of substantially straight, non-overlapping segments having ends;

the ends of respective pairs of the plurality of segments connected to each other, the segments not connected at any point intermediate their ends;

each circular member capable of retaining a compressed configuration while mounted onto an outer surface of a balloon catheter until application of a radial force to form an expanded configuration; and wherein each segment is aligned generally parallel to a longitudinal axis of the balloon catheter, when in a compressed configuration mounted on an outer surface of a balloon catheter.

17. The stent of claim 16, wherein the segments have a generally hexagonal cross-section.

18. The stent of claim 16, wherein the segments have a generally rectangular cross-section.

19. The stent of claim 16, wherein the segments have a generally round cross-section.

20. The stent of claim 16, wherein the generally circular members are not connected to each other.

21. The stent of claim 16, wherein the generally circular members are formed from a toroid.

22. The stent of claim 16, wherein all segments are aligned in a generally same direction, when in a compressed configuration mounted on an outer surface of a balloon catheter.

23. The stent of claim 16, wherein all segments are aligned generally parallel to a longitudinal axis of the stent, when in a compressed configuration mounted on an outer surface of a balloon catheter.

24. A stent delivery system comprising:

a delivery catheter having a balloon portion and a longitudinal axis;

a balloon-expandable stent mounted on the balloon portion and including a plurality of plastically deformable substantially straight segments having opposed ends, and arranged circumferentially around the balloon catheter; and each segment being connected to adjacent segments at its ends by curved members, each segment not connected to the adjacent segments at any point intermediate its ends, each curved member having substantially the same cross-section as the segments, wherein the balloon-expandable stent is capable of retaining a compressed configuration while mounted on the balloon catheter with each segment being oriented substantially parallel to the longitudinal axis when in the compressed configuration.

25. The stent delivery system of claim 24, wherein the segments have a substantially rectangular cross-section.

26. The stent delivery system of claim 24, wherein the curved members connect circumferentially adjacent segments.

27. A stent delivery system comprising:

a delivery catheter having an inflatable balloon and a longitudinal axis;

a plurality of plastically deformable balloon-expandable endovascular support members, mounted on the inflatable balloon and capable of retaining a compressed configuration when mounted on the balloon until application of a radial force by inflation of the balloon;

each plastically deformable balloon-expandable endovascular support member including a plurality of substantially straight segments having opposed ends, and arranged circumferentially around the inflatable balloon; and each substantially straight segment, of each plastically deformable balloon-expandable endovascular support member, being connected to circumferentially adjacent segments at its ends and not at any point intermediate of its ends; and wherein the plurality of endovascular support members are positioned along the inflatable balloon for simultaneous deployment.

28. The stent of claim 27, wherein the segments have a generally rectangular cross-section.

29. The stent of claim 27, wherein the segments have a generally round cross-section.

30. The stent as defined in claim 27, wherein the connections of opposed ends defines a series of upper and lower turns alternating in a circumferential direction.

* * * * *

UNITED STATES PATENT AND TRADEMARK OFFICE
CERTIFICATE OF CORRECTION

| | | |
|---|---|---|
| PATENT NO. | : 6,344,053 B1 | Page 1 of 1 |
| DATED | : February 5, 2002 | |
| INVENTOR(S) | : Michael D. Boneau | |

It is certified that error appears in the above-identified patent and that said Letters Patent is hereby corrected as shown below:

<u>Title page,</u>
Related U.S. Application Data, delete "which is a division of application No. 07/398,180, filed on August 24, 1999, now Pat. No. 5,292,331." and substitute -- which is a division of application No. 07/398,180, file on August 24, 1989, now Pat. No. 5,292,331. -- therefor.

Signed and Sealed this

Twenty-second Day of October, 2002

*Attest:*

*Attesting Officer*

JAMES E. ROGAN
*Director of the United States Patent and Trademark Office*